United States Patent [19]

Gordon et al.

[11] Patent Number: 5,612,178
[45] Date of Patent: Mar. 18, 1997

[54] METHOD OF QUANTITATIVE ENZYME DETERMINATION

[75] Inventors: Julian Gordon, Lake Bluff; Andreas A. Kapsalis, Evanston; Richard E. Thompson, Libertyville, all of Ill.

[73] Assignee: Abbott Laboratories, Abbott Park, Ill.

[21] Appl. No.: 933,971

[22] Filed: Aug. 24, 1992

Related U.S. Application Data

[63] Continuation of Ser. No. 117,278, Nov. 5, 1987, abandoned.

[51] Int. Cl.$^6$ .................. C12Q 1/00; C12Q 1/48; C12Q 1/34; C12Q 1/26
[52] U.S. Cl. .................. 435/4; 422/56; 435/15; 435/18; 435/25; 435/805
[58] Field of Search .................. 435/4, 15, 18, 435/25, 805; 436/517; 422/56, 57, 71

[56] References Cited

U.S. PATENT DOCUMENTS

| 3,875,014 | 4/1975 | Forgione | 435/805 X |
| 4,042,335 | 8/1977 | Clement | 23/253 TP |
| 4,235,601 | 4/1980 | Deutsch et al. | 422/71 X |
| 4,298,688 | 11/1981 | Kallies | 435/14 |
| 4,629,688 | 12/1986 | Bolguslaski et al. | 435/174 X |

FOREIGN PATENT DOCUMENTS

| 2433750 | 7/1979 | France . | |
| 8702774 | 5/1987 | WIPO | 435/805 |

Primary Examiner—David M. Naff
Attorney, Agent, or Firm—David L. Weinstein

[57] ABSTRACT

Methods and kits are provided for the quantitative determination of the presence of an enzyme analyte in a sample by determination of the rate of analyte catalyzed reaction on a chromatographic medium. The methods may be used to determine both steady state and non-steady state enzyme reaction kinetics and provide a physical record reflecting the same. In a preferred embodiment, an analyte enzyme in a sample to be analyzed is immobilized at a reaction site on a chromatographic medium, the chromatographic medium is contacted with a solution containing a substrate, the solution is transported on the chromatographic medium to the reaction site where the analyte enzyme catalyzes the reaction of the substrate to produce a detectable reaction product at a rate related to the amount of enzyme present, and the solution and reaction product are transported from the reaction site to a detection region formed by a length of the chromatographic medium downstream from the reaction site. Transport continues until the solution reaches the end of the chromatographic medium or until the quantity of solution is exhausted.

6 Claims, 4 Drawing Sheets

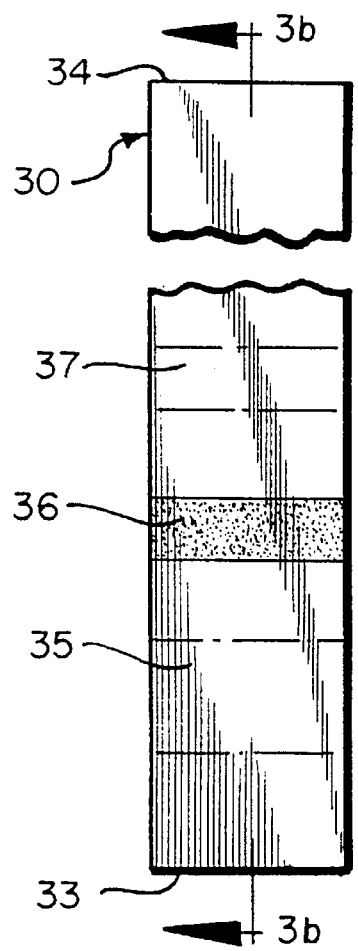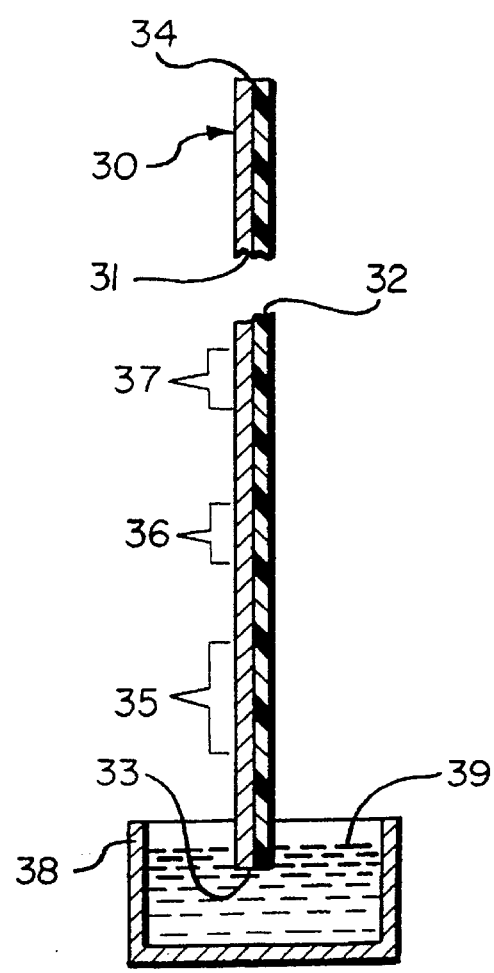

METHOD OF QUANTITATIVE ENZYME DETERMINATION

This application is a continuation of application Ser. No. 07/117,278, filed Nov. 5, 1987, now abandoned.

BACKGROUND OF THE INVENTION

The present invention relates generally to methods and devices for the quantitative determination of the presence of an enzyme in a sample by means of an analyte catalyzed reaction to form a reaction product. More specifically, the invention relates to methods wherein the analyte enzyme is immobilized at a reaction site on a chromatographic medium and substrates and cofactors for the analyte catalyzed reaction and products of that reaction are transported to and from the site by means of chromatographic solvent transport.

Methods known in the art for the detection of enzyme analytes in a sample generally involve contacting the sample to be analyzed with a mixture of substrate and cofactor materials the reaction of which is catalyzed by the analyte enzyme. The presence of the analyte in the sample may be determined by observation of the rate of production of a reaction product or consumption of a reactant (substrate or cofactor) as a consequence of the analyte-catalyzed reaction. Where the rate of production of a product of the reaction is used to indicate the presence of an enzyme, the product may be detected visually or spectrophotometrically. Alternatively, where a reaction product is not readily detectable by visual or spectrophotometric means, it may be detected by being subjected to one or more subsequent reactions which yield a readily detectable reaction product. Such reactions frequently involve activation of a dye precursor material. Where the rate of consumption of a reactant is used to indicate the presence of an enzyme, that reactant should be detectable visually or spectrophotometrically. A commonly used reactant is the cofactor nicotine adenine dinucleotide (NADH) which is detectable spectrophotometrically (at 340 nm) or fluorometrically (at 410 nm). The cofactor is oxidized in many enzyme catalyzed reactions to $NAD^+$ which does not emit the characteristic spectrophotometric or fluorometric signal. Many analyte catalyzed reactions are therefore followed by tracking the disappearance of NADH.

For example, methods are known for the detection of the enzyme alanine aminotransferase (ALT) increased blood levels of which are associated with hepatitis. Of interest to the present invention is the disclosure of Murray, Methods in Clinical Chemistry, pp. 1062–1065, Pesce & Waplan, eds., Mosby Publishing Co., St. Louis, Mo. (1987). ALT catalyzes the transamination reaction of L-alanine with alpha-ketoglutarate to produce pyruvate and L-glutamate. According to one widely used procedure for the detection of ALT, serum is incubated with L-alanine and alpha-ketoglutarate and after a measured length of time the reaction is stopped and the newly formed pyruvate is reacted with dinitrophenylhydrazine (DNPH) to form the corresponding hydrazone. The reaction mixture is then alkalinized to produce a blue color caused by the anion form of the hydrazone. The colorimetric procedure suffers from limited linearity as a consequence of feedback inhibition of the ALT by pyruvate. According to another procedure, NADH is incorporated in the reaction medium as is lactate dehydrogenase. The lactate dehydrogenase catalyzes the conversion of pyruvate to lactate with the simultaneous oxidation of reduced NADH to oxidized $NAD^+$. The disappearance of NADH is followed spectrophotometrically or fluorometrically.

Similar methods are known for the detection of the enzyme aspartate aminotransferase (AST) increased blood serum levels of which are associated with acute myocardial infarction, acute pancreatitis, viral and toxic hepatitis and acute cirrhosis. AST catalyzes the transamination reaction of aspartate and alpha-ketoglutarate to oxaloacetate and glutamate. Methods for the detection of this enzyme involve incubation of a sample to be tested with a solution containing aspartate, alpha-ketoglutarate and 2,4-dinitrophenylhydrazine such that the AST catalyzed production of oxaloacetate is coupled with the formation of a 2,4-dinitrophenyl-hydrazone-derivative which absorbs light at 520 nm. The presence of AST in the sample fluid is thus indicated by a color signal which can be measured spectrophotometrically or may be compared with a color chart to provide a semiquantitative indication of the presence of the AST. Similar procedures are known where the 2,4-dinitrophenylhydrazone dye precursor is replaced by an azozene dye which is capable of reacting with oxaloacetic acid. Still other methods for AST detection have become known involving the conversion of oxaloacetate to malate in a reaction utilizing malate dehydrogenase with NADH and $NAD^+$. Such analytical reactions may be carried out in containers such as test tubes and microtitre wells but may also be carried out on absorbent dip strips.

Of interest to the present invention is the disclosure of Forgione, U.S. Pat. No. 3,875,014 which discloses test indicators for the determination of AST concentrations in sera utilizing aspartic acid, alpha-ketoglutaric acid and a diazonium salt according to the reactions disclosed above. The test indicator comprises a pair of porous strips, adhered to each other with an adhesive which is selectively permeable to oxaloacetic acid, the first of which comprises the substrates L-aspartic acid and alpha-ketoglutaric acid. The second comprises a dried diazonium salt. The indicator is contacted with sera which, if it contains AST, catalyzes the reaction of the substrates to form oxaloacetic acid. Any oxaloacetic acid formed thereby then diffuses to the second strip and activates a color reaction with the diazonium salt.

The various assay methods for the quantitative detection of enzyme analytes tend to be limited in their accuracy by the nature of the kinetics of the enzyme catalyzed reaction. Such assays typically contact a sample containing an unknown amount of enzyme with substrates for that enzyme and determine the quantity of product produced by that reaction over a given period. The amount of product is indicative of the average rate of reaction which is itself related to the quantity of enzyme in the sample. The use of average rates of reaction to determine the quantity of enzyme present is limited by the fact that under typical assay conditions, such reactions do not generally have constant reaction rates. Enzyme catalyzed reactions carried out in a fixed volume of substrate/cofactor solution are affected by a number of startup and concentration effects which affect the rate of reaction. Typically, enzyme catalyzed reactions are characterized by a low start-up rate before reaching a "steady state." As the reaction proceeds and members of the enzyme substrate/cofactor group are consumed and their concentration diminishes, the reaction rate will slow. The rate of reaction will also be retarded as a consequence of feedback inhibition by accumulation of reaction products. Where the analyte catalyzed reaction is terminated by a change in reaction conditions or addition of an inhibitor, cessation of the reaction may not be entirely instantaneous thus adding additional uncertainty into the determination of average reaction kinetics. The true steady state reaction kinetics of the analyte catalyzed reaction may therefore vary significantly from the average reaction rate indicated by evaluation over a finite time period. Determinations of enzyme concentrations based on determinations of average reaction rates will thus be inaccurate to the degree that steady state reaction kinetics differ from average reaction rates. It is therefore desired to produce an assay method capable of evaluating the steady state reaction kinetics of a given reaction and preferably the instantaneous kinetics at any time.

SUMMARY OF THE INVENTION

The present invention relates to a method for the quantitative determination of the presence of an enzyme analyte in a sample by determination of the rate of analyte catalyzed reaction of controlled amounts of a substrate/cofactor group. Specifically, the presence of the analyte enzyme may be determined by catalysis of the reaction of members of a substrate/cofactor group, the method including the steps of; (a) immobilizing the analyte enzyme present in a quantity of the sample to be analyzed on a chromatographic medium, (b) contacting the chromatographic medium with a solution comprising members of a substrate/cofactor group, reaction of which to form at least one reaction product is catalyzed by the analyte enzyme at a rate related to the amount of enzyme present, (c) transporting the solution to the reaction site and reacting the substrate/cofactor group members in the presence of the enzyme to form a reaction product, (d) transporting the solution and the reaction product from the reaction site to a detection region downstream from the reaction site, and (e) determining the rate of the enzyme catalyzed reaction by determining (i) the rate of consumption of a member of the substrate/cofactor group or (ii) the rate of production of a reaction product. The rate of production of the reaction product may be determined by subjecting the product to one or more additional reactions and by determining (i) the rate of consumption of a reactant in said additional reaction or reactions or (ii) the rate of production of a product of said additional reaction or reactions. The rate of consumption of reactants or production of products may be determined by determining the concentration of the reactant or product at a selected site in the detection region. The methods of the invention may be used to determine both steady state and non-steady state enzyme reaction kinetics. The invention further provides kits for the practice of methods of the invention.

BRIEF DESCRIPTION OF THE DRAWINGS

FIGS. 1a and 3a are front plan views of two different forms of the test device of the present invention;

FIGS. 1b and 3b are cross-sectional views of the test devices shown in FIGS. 1a and 3a respectively, taken along lines 1b—1b and 3b—3b;

DETAILED DESCRIPTION

Figure 1A:
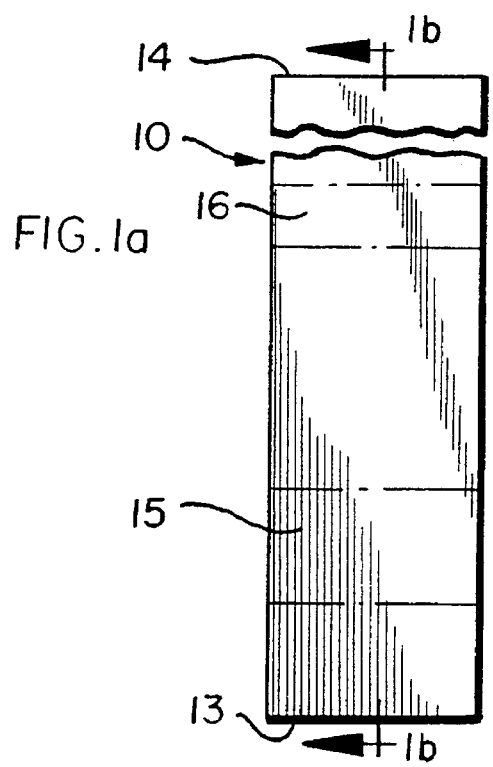

The present invention provides improved methods for the quantitative determination of the presence of an enzyme in a sample wherein the presence of the enzyme is determined by the enzyme catalyzed reaction of members of a substrate/cofactor group. The methods of the invention avoid the limitations of assay methods wherein the concentration of the analyte enzyme is determined by determination of the average rate of analyte catalyzed reaction over a finite period. The invention further avoids the limitations of those methods wherein incubation of the sample with the assay reagents must be timed to provide meaningful results. Instead of contacting the analyte containing sample with a fixed volume of substrate/cofactor containing solution in which the concentrations of reactants and products change during the course of the enzyme catalyzed reaction, the present invention immobilizes the enzyme present in the sample solution at a reaction site and continuously transports, fresh substrate/cofactor containing solution to the reaction site. In addition, solution containing reaction products and unreacted substrate/cofactor materials are transported from the reaction site and along a length of chromatographic medium in order that the concentration of products and reactants remains essentially constant at the reaction site. Transport of the solution containing unreacted members of the substrate/cofactor group and the products of the reaction is such that the concentration of reaction product and/or substrate/cofactor group members present at any point along that length is indicative of the rate of reaction at a specific time as determined by the quantity of bound enzyme, the geometry of the enzyme spot and the solution flow rate.

According to practice of the invention, a chromatographic medium is provided, preferably in the form of a strip. A quantity of the sample to analyzed is contacted with the chromatographic medium at a reaction site and any enzyme present in the sample is immobilized at that site. The chromatographic medium is then contacted with a chromatographically mobile solution with pH and ionic conditions selected for the specific reaction system including members of a substrate/cofactor group, which are consumed to produce a reaction product in a reaction catalyzed by the analyte enzyme. The solution including the members of the substrate/cofactor group is chromatographically transported along the chromatographic medium to the reaction site, where the enzyme substrates and cofactors are consumed in a reaction catalyzed by the analyte enzyme to form one or more reaction products. These products, along with the unreacted components of the substrate/cofactor group present in the quantum of fluid transported to the reaction site are then transported from the reaction site along the chromatographic medium to and through a detection region until the transport ceases. Such transport ceases either when the solvent is removed from the first end of the chromatographic medium or when the chromatographic medium is saturated such as when the materials reach the second end of the chromatographic medium.

Because of the constant flow of unreacted solution to and reacted solution from the reaction site, the concentration of substrates, cofactors and reaction products is substantially constant at that site. Feedback inhibition of the analyte catalyzed reaction will be substantially avoided as will the kinetic effects resulting from varying concentrations of the enzyme substrates and cofactors. With the exception of initial rates as a consequence of start-up effects, the rate of enzyme catalyzed reaction at the reaction site will generally be essentially constant. Under suitable conditions of substrate/cofactor excess, the reaction rate in the steady state will be directly related to the analyte enzyme concentration. The concentration of substrates, cofactors and reaction products in the solution flowing from the reaction site will be directly related to the rate of the enzyme catalyzed reaction at that site. Thus, the concentrations of reaction product, enzyme substrates and cofactors along the chromatographic pathway downstream of the reaction site provide a chronological record of the rate of enzyme catalyzed reaction at the reaction site over a period of time. The invention is therefore not only useful for determination of unknown concentrations of enzymes, but also for the study of enzyme kinetics more generally.

Determination of the concentration of a member selected from the group consisting of reaction products and enzyme substrates and cofactors along the detection region will therefore under controlled reaction conditions indicate the concentration of the enzyme analyte present in the sample. Typically, a site along the detection region, the complete region itself or the complete region excluding a small region near the second end where the product and substrate/cofactor member concentrations would reflect non-steady state reaction kinetics, would be selected for analysis to determine the concentration of products formed and reactants consumed during steady state reaction of the substrates and cofactors. Nevertheless, start-up or other unusual reaction kinetics of the reaction system may be analyzed by determination of the quantities of product present at sites along the detection region corresponding to such reaction kinetics.

It is frequently the case that the reaction products of the analyte catalyzed reaction are not readily detectable by visual or spectrophotometric means. In such cases it is desirable to couple one or more additional reactions to the analyte catalyzed reaction in order to produce a product or consume a reactant which is readily visually or spectrophotometrically detectable. Additional reagents may be incorporated into the substrate/cofactor containing solution which react with products of the analyte catalyzed reaction in a coupled reaction to consume a detectable reactant or produce a detectable reaction product. Coupled reactions are sequential in that one or more products of the first reaction is a reactant in the second. Typically, a reaction solution for carrying out a pair of coupled reactions will contain all reactants for the second reaction except the one product of the first. Thus, in the absence of the analyte enzyme to catalyze the first reaction, no reactants will be consumed or products produced by the second. The coupled reaction is preferably such that the reactants present in the substrate/cofactor containing solution may readily react to completion with one or more of the products of the analyte catalyzed reaction under the conditions present at the reaction site. Moreover, it is also preferred that the rate of the coupled second reaction not be rate limiting.

Where the coupled additional reaction proceeds spontaneously in the presence of the product of the analyte catalyzed reaction, the second reaction can and will take place at the reaction site or slightly downstream thereof. The concentration of the detectable products produced by this reaction, or alternatively detectable reactants consumed in this reaction, may accordingly be determined at locations downstream of the reaction site.

There are systems, however, where the coupled additional reaction does not spontaneously proceed in the presence of the product of the analyte catalyzed reaction. In such cases, it is necessary to catalyze the additional reaction in order that it proceed to completion. In order to utilize such coupled reaction systems, the invention provides assay devices where an enzyme or other catalyst is immobilized at a second reaction site at or preferably downstream of the first reaction site where the analyte enzyme is immobilized.

According to the practice of this aspect of the invention, the solution comprising members of the substrate/cofactor group and any reactants in the additional reaction is transported to the first reaction site where the analyte enzyme catalyzes the reaction of the members of the substrate/cofactor group to form one or more reaction products. Those reaction products along with unreacted members of the substrate/cofactor group and reactants for the additional reaction are contacted with the catalyst for the coupled additional reaction either at the first reaction site or at the second reaction site downstream therefrom. The catalyst then catalyzes reaction of a product of the analyte catalyzed reaction in a reaction which alternatively consumes a visually or spectrophotometrically detectable reactant or produces a similarly detectable product. The reaction conditions and quantities and identities of reagents are preferably selected such that the product of the analyte catalyzed reaction is completely consumed.

Where the reaction of the product of the analyte catalyzed reaction is quantitative and complete, the quantity of that first reaction product and hence the concentration of the analyte enzyme may be determined by the quantity of detectable reactant or product which is transported downstream from the second reaction site. Because the rate of the coupled additional reaction corresponds to that of the analyte catalyzed reaction, the kinetics of the analyte catalyzed reaction and hence the concentration of the analyte enzyme may be determined by observation of the coupled reaction.

Single Reaction Site Device

Figure 1B:
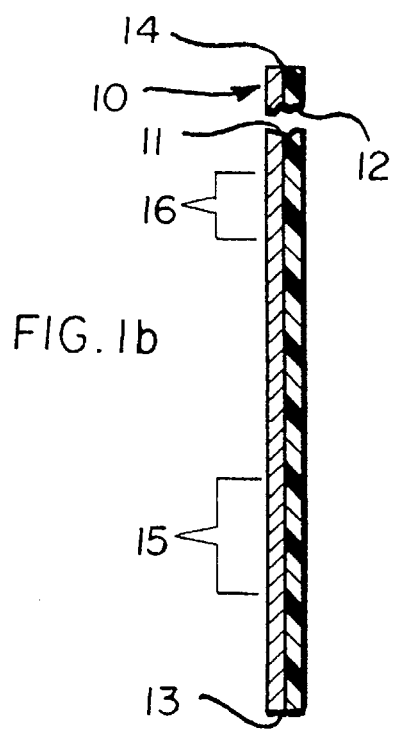
Figure 1C:
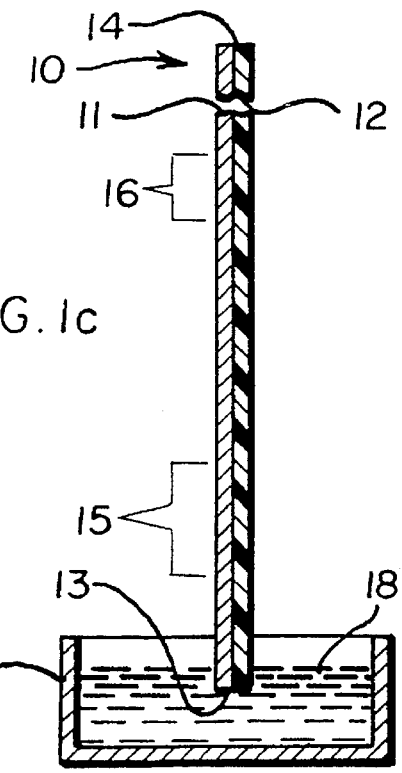
FIG. 1c is a cross-sectional view of the test device shown in FIG. 1a in contact with a volume of substrate/cofactor solution.

Referring to the drawing, FIGS. 1a, 1b and 1c depict a single reaction site test device (10) for the quantitative determination of the presence of an enzyme in a sample comprising a length of a chromatographic medium (11) which is attached to an inert support strip (12). The chromatographic medium (11) has a first end (13) at which chromatographic transport begins and a second end (14) at which chromatographic transport ends. The chromatographic medium (11) comprises a reaction site (15) disposed toward the first end (13) of the chromatographic material and a detection region (16) disposed between the reaction site (15) and the second end (14) of the chromatographic material. It should be noted for this and the other figures that the broken lines near the second end (14) indicate an extended distance between those that feature and the reaction site (15) which provide for chromatographic transport of substrate-cofactor materials and reaction products well beyond the reaction site (15).

According to a procedure for use of device (10) of FIGS. 1a, 1b and 1c, a liquid sample of the material to be analyzed for the presence of an enzyme is applied to the reaction site (15). The device (10) is then contacted at its first end (13) with the contents of a container (17) holding a solution (18) comprising members of a substrate/cofactor group, reaction of which is catalyzed by the analyte enzyme. The substrate/cofactor containing solution then progresses through the length of the chromatographic medium (11) to the reaction site (15) where the analyte enzyme acts to catalyze the reaction of the substrate/cofactor group members to form one or more reaction products. The solution comprising unreacted members of the substrate/cofactor group and any products of the analyte catalyzed reaction are transported from the reaction site toward the second end (14) of the chromatographic medium and to and through the detection region (16). The chromatographic transport of the solution containing reaction products and members of the substrate/cofactor group continues until the solution front reaches the second end (14) or until the quantity of solution is exhausted. The detection region is then evaluated to detect the concentration of a member selected from the group consisting of (i) members of the substrate/cofactor group and (ii) reaction products.

Figure 2A:
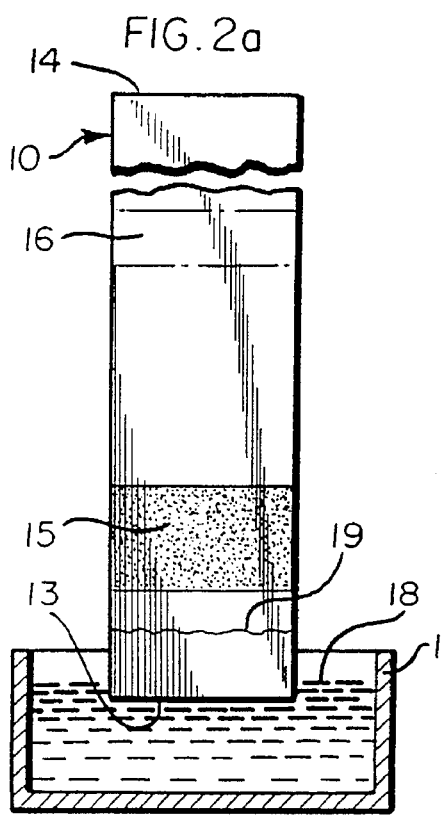
FIGS. 2a–2d are front plan views of the device depicted in FIG. 1a at different points in time according to practice of methods according to the invention.
Figure 2B:
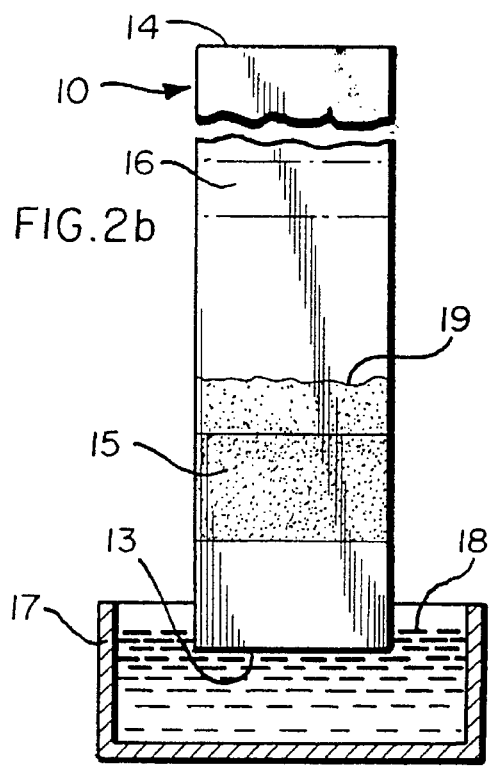
Figure 2C:
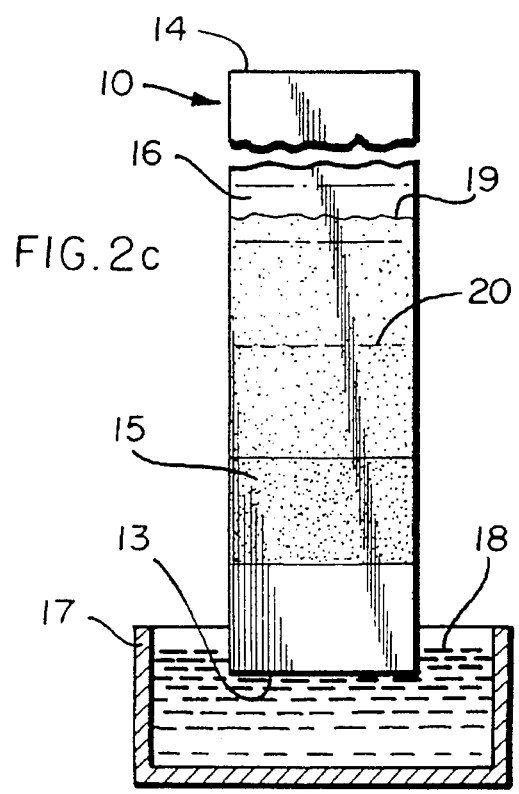
Figure 2D:
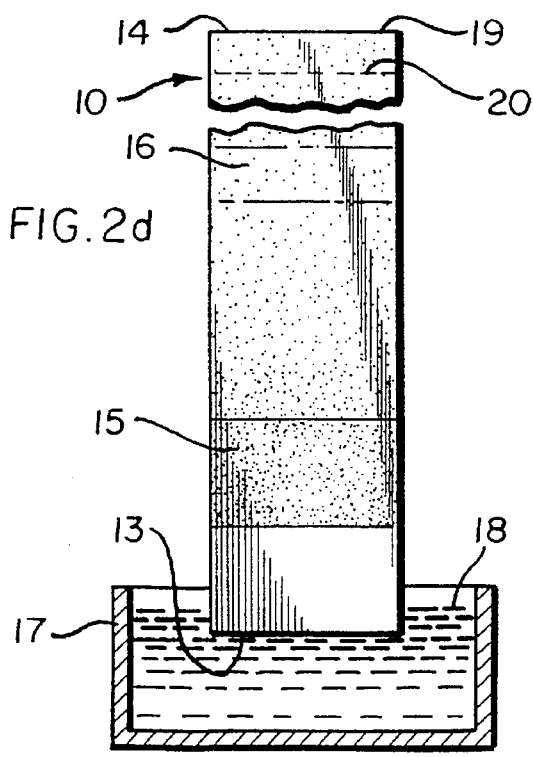
Figure 4:
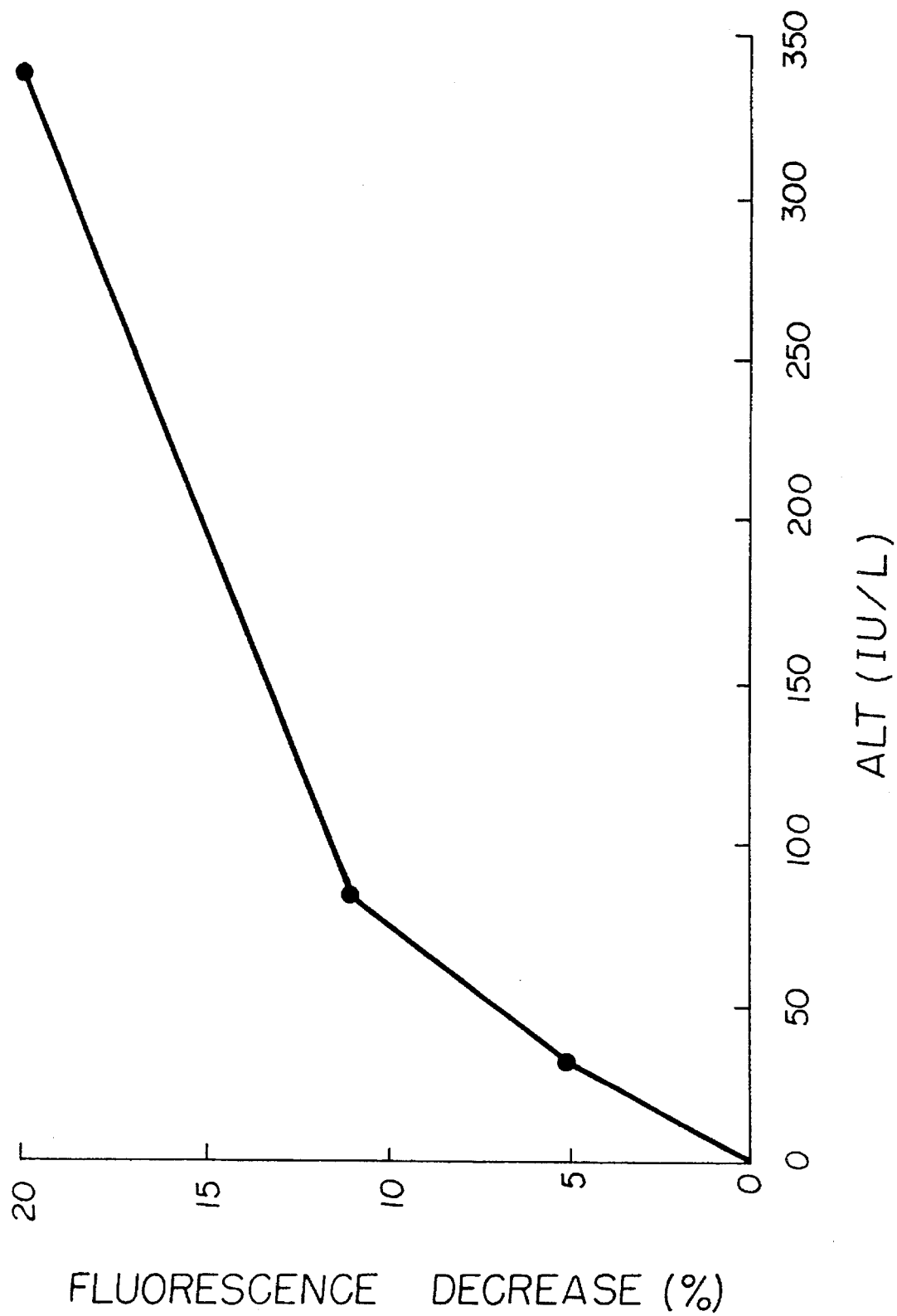
FIG. 4 is a graph depicting the relationship between concentrations of alanine aminotransferase and decreases in fluorescence caused by consumption of NADH cofactor in a device according to the invention.

FIGS. 2a–2d are front plan views of the device depicted in FIG. 1a. FIG. 2a depicts the device (10) which has been impregnated at reaction site (15) with a quantity of analyte containing sample. The device is being contacted with a solution (18) containing members of the substrate/cofactor group and the solution is being transported from the first end (13) of the chromatographic medium (11) with a solvent front (19) between the first end (13) and the reaction site (15). In FIG. 2b the solvent front (19) has passed through the reaction site (15) and the solvent downstream of the reaction site (15) contains quantities of a detectable reaction product produced during the start-up phase of the analyte catalyzed reaction of members of the substrate/cofactor group. In FIG. 2c the solvent front (19) has progressed farther toward the second end (14) of the chromatographic strip. At the same time, the analyte catalyzed reaction taking place at the reaction site (15) has passed through its startup phase and is progressing at a steady-state rate as indicated by the production of greater quantities of the detectable reaction product. While the transition from reaction start-up kinetics to steady-state kinetics is a gradual one and cannot truly be designated to occur at a specific time, such a demarcation between start-up and steady-state reaction kinetics is indicated by the steady-state reaction front indicated (20). In FIG. 2d, the solvent front (19) reaches the second end (14) of the chromatographic medium and chromatographic transport ceases. At this point, the steady-state reaction front (20) has passed beyond the detection region (16) such that the steady-state rate of analyte-catalyzed reaction and hence the quantity of analyte enzyme present may be evaluated by determination of the concentration of reaction product present.

Double Reaction Site Device

Referring to the drawing, FIGS. 3a and 3b depict a double reaction site test device (30) for the determination of the concentration of an enzyme analyte in a sample the device comprising a chromatographic medium (31) attached to an inert solid support (32). The chromatographic medium (31) has a first end at which chromatographic transport begins (33) and a second end (34) at which chromatographic transport ends. The chromatographic medium comprises a first reaction site (35) at which sample material containing analyte capable of catalyzing a first reaction is contacted and dried and a second reaction site (36) at which a catalyst is immobilized which catalyzes reaction of one or more products of the analyte catalyzed reaction in a second reaction. The chromatographic medium (31) further comprises a detection region (37) at which a member selected from the group consisting of a reactant or a reaction product produced at the second reaction site (36) is detected.

According to a procedure for use of device (30) of FIGS. 3a and 3b, a sample of the material to be analyzed for the presence of enzyme is applied to the first reaction site (35). The device (30) is then contacted at its first end (33) with the contents of a container (38) holding a solution (39) comprising members of a substrate/cofactor group, reaction of which is catalyzed by the analyte enzyme and also including reagents for reaction with a product of the analyte catalyzed reaction. The substrate/cofactor solution then progresses through the length of the chromatographic medium (31) to the first reaction site (35) where analyte enzyme acts to catalyze the reaction of the substrate/cofactor group members to form a reaction product. The solution containing unconsumed members of the substrate/cofactor group, any products of the analyte catalyzed reaction and any reagents for reaction with a product of the analyte catalyzed reaction are transported from the first reaction site to the second reaction site (36). The catalyst immobilized at the second reaction site (36) then catalyzes the reaction of the first product of the analyte catalyzed reaction to produce one or more second reaction products. The second reaction products along with unreacted members of the substrate/cofactor group and any reagents for reaction with the product of the analyte catalyzed reaction are then chromatographically transported from the second reaction site (36) toward the second end (34) of the chromatographic medium (34) and to and through the detection region (37). The chromatographic transport of the solution continues until the solution front reaches the second end (34) or until the quantity of substrate/cofactor solution is exhausted. The detection region (37) is evaluated to detect the amount of a member selected from the group consisting of (i) the products of the second reaction and (ii) reactants of the second reaction.

Chromatographic Media

Media useful with the present invention include not merely chromatographic media which are, according to the strictest sense of the term, useful for the separation of materials as a result of differential rates of transport but also include materials generally which are useful for solvent transport of the various reagents and reaction products used with the present invention. Suitable chromatographic media include those substrate materials having capillarity and the capacity for solvent transport of substrates, cofactors and reaction products. The chromatographic media used with the invention are preferably in the form of strips but may be fashioned into a variety of sizes and shapes as would be apparent to those of skill in the art. A wide variety of chromatographic materials such as woven and non-woven fibrous materials used for paper chromatography are suitable for use with the invention. Particularly preferred is the use of microporous or microgranular thin layer chromatography substrates as the use of such materials improves the speed and resolution of the assays according to the invention. Other suitable media include chemically modified materials such as reversed-phase high performance-thin layer chromatographic media or sulfated media. Such materials provide the increased potential for separation of reactants and reaction products where such is desirable. Microporous nitrocellulose materials are particularly preferred with the use of a microporous nitrocellulose material with a pore size of 3 µm designated Type SSWP (Millipore Corp., Bedford, Mass.) being most preferred. The materials should preferably be inert and generally not react physically or chemically with any of the substrates, cofactors or reaction products.

Because the chromatographic medium of the device is preferably chemically inert, it may have to be activated at any reaction site where it is desired to immobilize an analyte enzyme or a catalyst for catalysis of a coupled second reaction against solvent transport. Various methods will be required to render the reagent immobilized according to the particular chemical nature of the reagent. Generally, when the media is nitrocellulose or a mixed nitrocellulose ester, no special chemical linkage is required for the immobilization of enzymes. Sample containing the analyte enzyme is applied to the chromatographic media and may be dried after ten to fifteen minutes at room temperature. Enzymes present in the sample will be immobilized against solvent transport at the reaction site and will generally maintain full or substantial enzymatic activity. Where the assay utilizes a pair of coupled reactions, the second reaction being catalyzed, it is necessary to immobilize a catalyst for the coupled second reaction at a second reaction site. It is preferred that the catalyst of the coupled second reaction be an enzyme whereby the catalyst may be immobilized at that site by the same procedure through which the analyte enzyme is immobilized at the first reaction site.

Enzymes

It is contemplated that the present invention may be utilized for the quantitative detection of enzymes generally. Enzymes for which the present invention is believed to be particularly suitable in analysis of, include alanine aminotransferase (ALT), aspartate aminotransferase (AST), lactate dehydrogenase (LDH), acid phosphatase, aldolase, alkaline phosphatase, alpha-naphthyl butarate esterase, alpha-1 trypsin, amylase, angiotensin converting enzyme, ceruloplasmin, chloracetate esterase, creatine kinase, cholinesterase, galactose-1-phosphate uridyl transferase, gamma glutamyl transferase, hemoglobin (as an oxidase), lipase, lysozyme, 2'5'-adenylate phosphodiestorase, 2'5'-adenylate synthetase, 5' nucleotidase, renin, trypsin and numerous others. Enzymes which may be assayed according to the present invention are limited only to the extent that selected enzymes may not be immobilized on suitable chromatographic media or lose substantially all enzymatic activity when so bound. That certain enzymes may lose some of their activity when immobilized at the first reaction site does not detract from the utility of the invention because such activity loss can be accounted for when evaluating assay results as would be well within the capabilities of one of skill in the art. Enzyme containing samples which may be analyzed according to the methods of the invention include various biological materials including but not limited to blood, serum, plasma, urine, saliva, stools, tears, throat swabs, wound exudates, sweat, cells, cell lysates, cell supernatants, bacteria and bacterial media.

Substrate/Cofactor Systems

Members of substrate/cofactor groups of reagents susceptible to reaction by analyte enzymes and suitable for use with the present invention are selected according to the specific nature of the enzyme to be analyzed for. Such reaction systems are generally known to the art and may be readily applied according to the methods of the present invention. In general, single and coupled enzyme reaction systems useful according to conventional test-tube or dip strip methodologies may be utilized according to the invention. Suitable systems include those where substrates for enzyme catalyzed reactions or cofactors for such reactions are reacted to yield a visually or spectrophotometrically detectable reaction product such as a dye. Alternatively, the enzyme substrate or a cofactor of the analyte catalyzed reaction may itself be visually or spectrophotometrically detectable (such as the cofactor NADH) but is consumed in the course of the enzyme catalyzed reaction.

According to certain embodiments of the invention, where neither a member of the substrate/cofactor group of reagents for an enzyme catalyzed reaction nor a product of that reaction are readily detectable by visual or spectrophotometric means, the analyte catalyzed reaction may be coupled to a second reaction which either consumes a readily detectable reactant or produces such a product. Litman, et al., U.S. Pat. No. 4,533,629, issued Aug. 6, 1985, the disclosure of which is hereby incorporated by reference, discloses a number of coupled enzyme reaction systems utilized to produce signals in enzyme labelled immunoassays. Such coupled reaction systems frequently utilize hydrolysis or oxidation-reduction reactions to activate dye precursors. According to some methods, substrates are oxidized to produce hydrogen peroxide which then reacts with dye precursors to activate a detectable dyestuff. The substrate/cofactor group containing solutions may be combined with other reagents such as stabilizers, inhibitors and the like. Where the analyte catalyzed reaction is coupled to a second reaction, the substrate/cofactor group containing solution may also comprise reagents for reaction with the product of the analyte catalyzed reaction. Such reagents may themselves be detectable and capable of being consumed in the coupled second reaction or may react with the product of the-analyte catalyzed reaction to produce a detectable reaction product.

EXAMPLE 1

According to this example, devices for the quantitative determination of the enzyme lactate dehydrogenase (LDH) were fabricated and used according to the methods of the invention. Microporous nitrocellulose material with a thickness of approximately 0.15 mm and a pore size of 3 µm (Millipore SSWP) was laminated to Mylar and adhesive (Monokote, Top Flite Models, Inc., Chicago, Ill.) at 60 to 65 C in a film dryer apparatus. The membrane and backing were cut to strips 0.3 cm wide and 8.5 cm long.

According to a method of using the above constructed devices, various dilutions of LDH (Sigma Chemical Co., St. Louis, Mo.) in a solution comprising 0.8 mg/ml bovine serum albumin were prepared. Aliquots comprising 2 µl of the LDH solution were impregnated onto the chromatographic strips at a reaction site 1 cm from a first end. The strips were then dipped at their first end in a solution comprising 0.1M phosphate buffer, pH 7.8, pyruvate, 0.22 mM reduced beta-nicotine adenine dinucleotide (NADH) and 1 mM sodium pyruvate. The running buffer was chromatographically transported along the strip until it reached the reaction site at which the LDH sample had been immobilized. There, the LDH catalyzed the reaction of pyruvate with NADH and a proton to form lactate and the oxidized form of nicotine adenine dinucleotide (NAD). These reaction products, along with the other components of the solution were chromatographically transported from the reaction site downstream along the chromatographic strip until the solution reached the end of the strip and the solvent transport stopped. The results were observed visually as the disappearance of fluorescence downstream of the reaction site as observed under an ultraviolet (375 nm) lamp.

EXAMPLE 2

According to this example, two reaction site devices for the quantitative determination of the enzyme ALT were fabricated and used according to the methods of the invention. Microporous nitrocellulose material with a thickness of approximately 0.15 mm and a pore size of 3 µm (Millipore SSWP) was laminated to Mylar and adhesive (Monokote, Top Flite Models, Inc., Chicago, Ill.) at 60° to 65° C. in a film dryer apparatus. The membrane and backing were cut to strips 0.3 cm wide and 8.5 cm long. To a second reaction site 2 cm from a first end of each of the strips was immobilized a 2 µl aliquot of the enzyme lactate dehydrogenase (LDH) (Sigma Chemical Co., St. Louis, Mo.).

According to a method of using the above constructed devices, various dilutions of ALT in a solution comprising 0.8 mg/ml bovine serum albumin (BSA) were prepared. The solutions were then analyzed for enzymatic activity by means of a clinical chemistry reagent (A-gent, Abbott Laboratories, North Chicago, Ill.). To a first reaction site located between the LDH impregnated site and the first end and 1 cm from the first end was impregnated 2 μl of the ALT containing solution. The enzyme samples were allowed to dry at the reaction site for ten to fifteen minutes.

The strips were dipped at their first end in a solution of solvent comprising 500 mM L-alanine, 0.3 mM reduced beta-nicotine adenine dinucleotide (NADH), 15 mM alpha-ketoglutarate, 0.1 mM pyridoxal-5-phosphate, 100 mM tris(hydroxymethyl)-aminomethane, 30.3 mM succinic acid and 2.26 mM sodium ethylene diamine tetraacetic acid (EDTA). The solvent was chromatographically transported along the strip until it reached the first reaction site at which the ALT sample had been immobilized. There, the ALT catalyzed the reaction of the L-alanine with the alpha-ketoglutarate to form pyruvate and L-glutamate. As the solvent continued to progress, these reaction products along with the unreacted enzyme substrates and cofactors and the other components of the running buffer were then chromatographically transported from the first reaction zone at which the ALT samples had been immobilized to the second reaction zone at which the LDH had been immobilized. As the pyruvate and other components of the solvent contacted the LDH immobilized at the second zone, the LDH catalyzed the reaction of pyruvate with the NADH and a proton to form lactate and the oxidized form of nicotine adonine dinucleotide (NAD$^+$). These products of the second reaction were then transported along the chromatographic medium for 3 to 4 cm until the chromatographic transport ceases. The oxidation of NADH to NAD$^+$ was followed visually as the disappearance of fluorescence downstream of the LDH reaction site was observed under an ultraviolet (375 nm) lamp. Fluid ahead of the front exhibited no fluorescence while fluid at the front corresponding to start-up kinetics showed a peak of fluorescence which diminished to a constant level (corresponding to steady-state kinetics) which then extend to the second reaction site.

While the fluorescence may be observed visually, it may also be observed spectrophotometrically with a thin layer chromatogram scanner such as (CAMAG Scanner II, CAMAG, Muttenz, Switzerland). The scanner uses an excitation wavelength of 365 nm and detection using a filter with cutoff of less than 420 nm.

From the foregoing description, one of skill in the art will recognize numerous changes and modifications of the invention to adapt it to particular usages. Consequently, only such limitations should be placed on the invention as appear in the following claims.

What is claimed is:

1. A method for the quantitative determination of the presence of an analyte enzyme in a sample comprising the steps of:

(a) immobilizing the analyte enzyme present in a quantity of sample to be analyzed at a reaction site on a chromatographic medium, (b) contacting said chromatographic medium with a solution comprising a substrate, (c) transporting said solution to said reaction site wherein said analyte enzyme catalyzes the reaction of said substrate to produce a detectable reaction product at a rate related to the amount of enzyme present;

(d) transporting said solution and said reaction product from said reaction site to a detection region comprising a length of said chromatographic medium downstream from said reaction site wherein transport continues until said solution reaches the end of said chromatographic medium or until the quantity of solution is exhausted, and wherein the production of said reaction product results in a continuous record of the rate of reaction, and (e) detecting a signal produced by (i) said substrate, (ii) said reaction product, or (iii) a reactant or product of one or more additional reactions of said reaction product, at a selected site in said detection region.

2. The method according to claim 1 wherein said selected site in the detection region contains said substrate which is consumed or said reaction product which is produced only during steady state reaction of the analyte enzyme.

3. The method according to claim 1 wherein said additional reaction or reactions are catalyzed by means of a catalyst immobilized at a second reaction site.

4. The method according to claim 3 wherein said catalyst is an enzyme.

5. The method according to claim 1 wherein said signal is detected visually or spectrophotometrically.

6. The method according to claim 5 wherein said signal is a color signal which is detected visually.

* * * * *

UNITED STATES PATENT AND TRADEMARK OFFICE
CERTIFICATE OF CORRECTION

PATENT NO. : 5,612,178
DATED : March 18, 1997
INVENTOR(S) : Gordon, et. al.

It is certified that error appears in the above-indentified patent and that said Letters Patent is hereby corrected as shown below:

Column 12, line 17, change "present;" to --present,--.

Signed and Sealed this

Twelfth Day of August, 1997

Attest:

BRUCE LEHMAN

Attesting Officer

Commissioner of Patents and Trademarks